(12) United States Patent
Mink et al.

(10) Patent No.: US 7,541,194 B2
(45) Date of Patent: Jun. 2, 2009

(54) DEVICE FOR COLLECTION AND ASSAY OF ORAL FLUIDS

(75) Inventors: Ronald W. Mink, West Linn, OR (US); Andrew S. Goldstein, Portland, OR (US); Robert C. Bohannon, Chapel Hill, NC (US)

(73) Assignee: Orasure Technologies, Inc., Bethelham, PA (US)

( * ) Notice: Subject to any disclaimer, the term of this patent is extended or adjusted under 35 U.S.C. 154(b) by 111 days.

(21) Appl. No.: 11/653,916

(22) Filed: Jan. 17, 2007

(65) Prior Publication Data

US 2007/0116597 A1  May 24, 2007

Related U.S. Application Data

(60) Division of application No. 09/973,956, filed on Oct. 11, 2001, now Pat. No. 7,192,555, which is a division of application No. 09/292,293, filed on Apr. 15, 1999, now Pat. No. 6,303,081, which is a continuation-in-part of application No. 09/280,269, filed on Mar. 29, 1999, now abandoned.

(60) Provisional application No. 60/079,958, filed on Mar. 30, 1998.

(51) Int. Cl.
G01N 33/53 (2006.01)

(52) U.S. Cl. ............... 436/514; 436/518; 436/162; 436/170; 436/810; 435/7.1; 435/7.94; 435/7.8; 435/7.9; 435/287.1; 435/287.2; 435/287.7; 435/974

(58) Field of Classification Search ........... 435/7.1, 435/7.94, 7.8, 7.9, 287.1, 287.2, 287.7, 974; 436/514, 518, 162, 170, 810
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,014,322 A | 3/1977 | Shah | |
| 4,275,149 A | 6/1981 | Litman et al. | |
| 4,277,437 A | 7/1981 | Maggio | |
| 4,313,734 A | 2/1982 | Leuvering | |
| 4,366,241 A | 12/1982 | Tom et al. | |
| 4,444,879 A | 4/1984 | Foster et al. | |
| 4,446,232 A | 5/1984 | Liotta | |
| 4,624,929 A | 11/1986 | Ullman | |
| 4,635,488 A | 1/1987 | Kremer | |
| 4,806,311 A | 2/1989 | Greenquist | |
| 4,855,240 A | 8/1989 | Rosenstein et al. | |
| 4,857,453 A | 8/1989 | Ullman et al. | |
| 4,868,108 A | 9/1989 | Bahar et al. | |
| 4,956,302 A | 9/1990 | Gordon et al. | |
| 5,103,836 A | 4/1992 | Goldstein et al. | |
| 5,120,643 A | 6/1992 | Ching et al. | |
| 5,160,486 A | 11/1992 | Schlipfenbacher et al. | |
| 5,211,182 A | 5/1993 | Deutsch et al. | |
| 5,260,031 A | 11/1993 | Seymour | |
| 5,268,148 A | 12/1993 | Seymour | |
| 5,334,502 A | 8/1994 | Sangha | |
| 5,376,337 A | 12/1994 | Seymour | |
| 5,380,492 A | 1/1995 | Seymour | |
| 5,393,496 A | 2/1995 | Seymour | |
| 5,425,377 A | 6/1995 | Callouette | |
| 5,479,937 A | 1/1996 | Thieme et al. | |
| 5,494,646 A | 2/1996 | Seymour | |
| 5,556,789 A | 9/1996 | Goerlach-Graw et al. | |

(Continued)

FOREIGN PATENT DOCUMENTS

EP    0323605 B1    1/1994
GB    2204398 A     11/1988

OTHER PUBLICATIONS

Anni. New York Acad. Sci., vol. 694; Saliva as a Diagnostic Fluid, Malamud and Tabak, eds., N.Y. Acad. Sci. Pub. (1993), Table of Contents.
Fundamental Immunology, W. E. Paul, ed., Raven Press, N.Y. (1993), Table of Contents.
Harlow and Lane (1988) Antibodies, A Laboratory Manual, Cold Spring Harbor Publications, New York, New York, Table of Contents.
U.S. Appl. No. 10/076,596 with currently pending claims.

*Primary Examiner*—Bao-Thuy L Nguyen
(74) *Attorney, Agent, or Firm*—Nixon Peabody LLP; Jeffrey A. Lindeman

(57) ABSTRACT

A device for collecting and transporting aqueous fluid from the oral cavity to a lateral chromatographic strip for test is disclosed. The lateral chromatographic strip is placed within and extend along a cavity defined in a housing. At least one inspection site to the lateral chromatographic strip is provided to enable inspection of selected sites on the lateral chromatographic strip for test results. A porous wick material protrudes from the housing to a collection site exterior of the housing at one end and communicates to the lateral chromatographic strip at the other end. The porous wick material has particulate construction, the particles adsorbing aqueous oral fluid to transport the fluid from the mouth to the lateral chromatographic strip without substantial absorption. The particles of the porous wick material are bound together to define a continuous interstitial volume for the flow of oral fluid to be transported and are treated to be hydrophilic to the adsorbed oral fluids. The porous wick material readily releases oral fluid to the lateral chromatographic strip. Prevention of reverse flow to the oral cavity from the lateral chromatographic strip naturally occurs due to the circuitous flow path of the porous wick material. A bite plate is coupled to the housing and insertable between the teeth of the patient to position the porous wick in the oral cavity for collecting the oral fluid. The bite plate is typically held in place by the occlusal force of the teeth, preferably the molars and/or the bicuspids, to position the porous wick in the buccal space. By observing the lateral chromatographic strip while the test device is in the mouth immediate test results are obtained.

26 Claims, 3 Drawing Sheets

U.S. PATENT DOCUMENTS

| | | |
|---|---|---|
| 5,569,608 A | 10/1996 | Sommer |
| 5,578,577 A | 11/1996 | Ching et al. |
| 5,591,645 A | 1/1997 | Rosenstein |
| 5,602,040 A | 2/1997 | May et al. |
| 5,609,160 A | 3/1997 | Bahl et al. |
| 5,611,995 A | 3/1997 | de Zoeten et al. |
| 5,622,871 A | 4/1997 | May et al. |
| 5,656,502 A | 8/1997 | MacKay et al. |
| 5,656,503 A | 8/1997 | May et al. |
| 5,695,929 A | 12/1997 | Goldstein |
| 5,714,341 A | 2/1998 | Thieme et al. |
| 5,714,389 A | 2/1998 | Charlton et al. |
| 5,741,662 A | 4/1998 | Madsen et al. |
| 5,820,826 A | 10/1998 | Moorman |
| 5,824,268 A | 10/1998 | Bernstein et al. |
| 5,830,410 A | 11/1998 | Thieme et al. |
| 5,965,453 A | 10/1999 | Skiffington et al. |
| 5,989,921 A | 11/1999 | Charlton et al. |
| 6,001,658 A | 12/1999 | Fredrickson |
| 6,046,057 A | 4/2000 | Nazareth et al. |
| 6,048,735 A | 4/2000 | Hessel et al. |
| 6,117,090 A | 9/2000 | Callouette |
| 6,140,136 A | 10/2000 | Lee |
| 6,146,590 A | 11/2000 | Mazurek et al. |
| 6,156,271 A | 12/2000 | May |
| 6,187,598 B1 | 2/2001 | May et al. |
| 6,228,660 B1 | 5/2001 | May et al. |
| 6,248,598 B1 | 6/2001 | Bogema |
| 6,352,862 B1 | 3/2002 | Davis et al. |
| 6,485,982 B1 | 11/2002 | Charlton |
| 6,534,320 B2 | 3/2003 | Ching et al. |
| 6,632,682 B1 | 10/2003 | Ziegelmaier |

DEVICE FOR COLLECTION AND ASSAY OF ORAL FLUIDS

CROSS-REFERENCE TO RELATED APPLICATIONS

This application is a divisional of U.S. patent application Ser. No. 09/973,956, filed Oct. 11, 2001 now U.S. Pat No. 7,192,555, which is a divisional of U.S. patent application Ser. No. 09/292,293, filed Apr. 15, 1999, now U.S. Pat. No. 6,303,081, which is a continuation-in-part of U.S. patent application Ser. No. 09/280,269, filed Mar. 29, 1999, now abandoned and which, in turn, claims priority from, U.S. Provisional Patent Application No. 60/079,958, filed Mar. 30, 1998, the entire contents of which are incorporated herein by reference.

FIELD OF THE INVENTION

This invention relates to the assay of oral fluids typically in lateral flow chromatography. A single unit, continuous in-line, one step rapid assay format suitable for oral specimen collection and testing is disclosed. More particularly, a hydrophilic capillary matrix is disclosed as a transport for oral fluids to a lateral chromatographic strip. This enables rapid assay of oral fluids while a disposable testing device is held in a patient's mouth.

BACKGROUND OF THE INVENTION

Numerous analytical methods have been developed for determining the presence or absence and/or quantifying the amount of various analytes in tissues and fluids of organisms. Currently most diagnostic testing is done with blood, urine, fecal material, or tissue biopsy. Testing based on these materials, however, entails substantial invasion of privacy and poses a significant safety hazard (particularly with the testing of blood). In contrast, the collection of oral fluid including saliva and/or mucosal transudate for testing entails relatively little invasion of privacy, is relatively safe, and can be accomplished rapidly with relative ease.

The use of oral fluid for detection purposes has been discussed in scientific and clinical research for some time. A multitude of researchers have investigated using oral fluid as a possible clinical specimen for diagnosis of specific disease states or altered metabolic activity (see, e.g., Ann. New York Acad. Sci., Vol. 694: Saliva as a Diagnostic Fluid, Malamud and Tabak, eds., N.Y. Acad. Sci. Pub. (1993)). There is a preponderance of evidence that suggests that oral fluids might be extremely useful samples for the detection of certain analytes. The basic technological premise is that analytes present in blood will pass through the oral mucosa and/or salivary glands into the oral cavity where they can be detected. Further it is assumed that the concentration of analyte in oral fluid will be indicative of the blood concentration. There is thus considerable interest in the development of devices for the collection, transport, and sample handling of oral fluids and in the development of oral fluid-based assays; in particular assays for various antibodies and metabolites.

Typically in tests performed with samples such as blood, urine, or fecal material, there is an ample supply of test material and high volumes of analytes are available for assay. In addition, since assays of such materials are performed outside the body, there is no issue of contamination of the body with assay reagents.

This is illustrated, for example, in the assay device described by de Zoeten et al., U.S. Pat. No. 5,611,995, issued Mar. 18, 1997. In this device an absorbing body is supplied with a handle and held in the stream of urine being expelled from the body. When the absorbing body is saturated, it is then inserted into a holding device having a test strip. The saturated pad comes into contact with a test strip, is compressed, and deposits urine to be tested on the test strip. A gap at the side of the hold device holding the test strip assures evaporation of excess fluid to prevent backflow along the test strip.

Previously described assays of biological samples, in particular assays for analytes in oral fluid, have typically required at least two different actions. First the sample, e.g., blood, or urine is collected. Then the collected sample is either stored, e.g., for later assay in a laboratory, or is assayed in or by an assay device which is typically a device other than the collection device. Such assays, requiring multiple components, are often expensive to manufacture and cumbersome for home use.

Moreover, particularly with respect to assaying oral fluid samples, oral fluid is often in short supply, particularly under circumstances where the test subject is stressed (e.g., when testing for drugs of abuse or life-threatening illnesses, which may make it difficult to use such multi-component assays).

When typical absorbent pads are used to recover oral fluid, the pads must typically be compressed to release the trapped oral fluid. The manipulations associated with the compression step can result in sample contamination. In addition, such a traditional pads have a significant void volume requiring that the sample often be collected in a volume significant greater than is actually required for analyte assay itself.

SUMMARY OF THE INVENTION

This invention provides improved devices and methods for one-step collection of oral fluid for detection and/or quantification of analytes in the oral fluid. The devices and methods require extremely low volumes of oral fluid, and require no subsequent sample manipulation after collection. Adequate sample collection is immediately verified and the risk of sample contamination is minimized. The assays are direct, rapid, and require no complicated steps. The devices and methods are therefore ideally suited for use in homes, in work or office settings, and generally do not require the presence of trained medical personnel.

Unlike prior art oral fluid collection devices that typically utilize an absorbent pad made of paper, cellulose, cotton or sponge and which require compression or centrifugation of the collection pad to release the oral fluid sample, the devices of this invention utilize a relatively rigid capillary matrix also referred to as a capillary matrix. The capillary matrix, when inserted into the oral cavity of a mammal (e.g., a human) rapidly wicks up oral fluid (e.g., via capillary action) and delivers it to the receiving area of a lateral flow chromatography strip. The oral fluid is rapidly released from the capillary matrix to the lateral flow chromatography strip without any manipulation (e.g., compression) of the matrix.

In one embodiment this invention provides an apparatus for lateral flow chromatography of an oral fluid. The apparatus comprises a capillary matrix having exposed a surface for insertion into an oral cavity; and a lateral flow chromatography strip where the lateral flow chromatography strip is attached to the capillary matrix such that when the capillary matrix is contacted to an oral mucosa in an oral cavity, the capillary matrix wicks up oral fluid and delivers the oral fluid to a receiving area of a lateral flow chromatography strip. In another embodiment, the apparatus comprises a capillary matrix having exposed a surface for receiving oral fluid; and a lateral flow chromatography strip where the lateral flow chromatography strip is in communication with the capillary matrix such that when the capillary matrix receives oral fluid, the capillary matrix wicks up the oral fluid and delivers the oral fluid to a receiving area of the lateral flow chromatography strip.

In a preferred embodiment, the capillary matrix is composed of a material different from the material comprising the lateral flow chromatography strip or the receiving area or sample pad of such a strip. The capillary matrix is composed of a material such that saturation of the capillary matrix with an oral fluid does not substantially alter the morphology of the capillary matrix. Thus, neither the average pore size nor the void volume of the capillary matrix is substantially altered. In addition, the volume of the capillary matrix is substantially constant. Saturation of the capillary matrix typically effects less than 30%, preferably less than 25%, more preferably less than 20% and most preferably less than about 15%, 10%, 5% or less than about even 1%. The capillary matrix preferably has an average pore size ranging from about 40 µm to about 250 µm, more preferably from about 60 µm to about 200 µm, and most preferably from about 80 µm to about 120 µm and a void volume of less than about 60 µL/cm$^3$. Particularly preferred porous matrix materials have pore sizes that range from about 45 µm to about 90 µm, from about 90 µm to about 130 µm, or from about 80 µm to about 120 µm. Preferred capillary matrix materials are plastics (e.g., porous matrices of a high density polyethylene (HDPE), an ultra-high molecular weight polyethylene (UHMW), a polypropylene (PP), a polyester, a polyvinylidene fluoride (PVDF), a polytetrafluoroethylene (PTFE), a nylon 6 (N6), or a polyethersulfone (PES)). The plastics may be hydrophilic or treated (e.g., with a surfactant such as sodium N-methyl cocoyl taurate) to be hydrophilic.

In a preferred embodiment, the capillary matrix, when contacted to an oral mucosa takes up oral fluid from the oral cavity and readily releases the oral fluid to the receiving area of the lateral flow chromatography strip in under about 5 minutes (preferably under about 2 minutes, more preferably under about 1 minute) without compression, altered air or fluid pressure, or other manipulation of the matrix material. The capillary matrix, when contacted to an oral mucosa takes up oral fluid from the oral cavity and releases the oral fluid to the receiving area of the lateral flow chromatography strip most preferably in under about 30 seconds. Under these conditions, the capillary matrix, is preferably saturated with oral fluid in under about 1 minute, and saturation typically utilizes less than about 300 µL of oral fluid. Generally speaking, the capillary matrix will released sufficient oral fluid to saturate the receiving area of the chromatographic strip.

The apparatus can optionally further include a blocking strip placed between the capillary matrix and the lateral flow chromatographic strip. The blocking strip can contain a blocking reagent (e.g., BSA, deoxycholate, sodium-n-lauroylsarcosine, etc.) and/or one or more buffers. In certain embodiments, the blocking strip can also prevent backflow of reagents from the lateral flow chromatography strip to the capillary matrix.

The apparatus can optionally further include a conjugate strip that contains one or more chromatography reagents (e.g., labeled microparticles). In addition, a single strip can double as a blocking strip and a conjugate strip.

The apparatus can further comprise a housing having a cavity, wherein the lateral flow chromatography strip extends into the cavity along the housing to an inspection site on the housing; and at least one inspection site from an exterior of the housing to the lateral chromatographic strip to enable visual inspection of reagents at selected sites on the lateral chromatographic strip. The housing can act as a handle for inserting the capillary matrix into the oral cavity. The housing can be fabricated out of any convenient material (e.g. HDPE, LDPE, PP, polystyrene, acrylic, polycarbonate, etc.).

In accordance with another embodiment, an apparatus for collection and lateral flow chromatography of an oral fluid comprises a lateral flow chromatography strip including a receiving area; and a capillary matrix having a surface. A bite portion is coupled to the capillary matrix and insertable between the teeth of a subject to position the surface of the capillary matrix for receiving an oral fluid of the subject. The capillary matrix is in communication with the lateral flow chromatography strip to wick up and deliver the received oral fluid to the receiving area of the lateral flow chromatography strip. In a specific embodiment, the bite portion comprises textured or non-textured surfaces for contacting the teeth, and is insertable between the teeth of the subject to optionally contact the tongue of the subject. The bite portion may include a saliva-stimulating substance selected from the group consisting of citric or other acids (e.g., tartaric, fumaric, ascorbic, malic, etc.) acid, salt, and natural sweetener (e.g. fructose, glucose, sucrose etc.) or artificial sweetener (e.g. NutraSweet™). The bite portion can optionally include other materials such as artificial or natural flavors and/or aromatic substances, and/or polysaccharides, gelatin, shellac, or other coating materials. The bite portion is connected to a housing having a cavity in which the lateral flow chromatography strip is at least partially disposed.

In accordance with yet another embodiment, an apparatus for collection and lateral flow chromatography of an oral fluid comprises a lateral flow chromatography strip including a receiving area; and a bite portion insertable between the teeth of a subject. The apparatus further comprises collection means coupled to the bite portion to contact an oral mucosa of the subject for receiving oral fluid of the subject, and in communication with the lateral flow chromatography strip for wicking up and delivering the received oral fluid to the receiving area of the lateral flow chromatography strip.

In another embodiment, this invention provides methods of detecting an analyte in the oral fluid of a subject. In preferred embodiments, the methods involve inserting the apparatus (collection devices) described herein into the oral cavity of said subject such that the bite portion of the apparatus is held between the teeth of the subject, retaining the apparatus in the oral cavity until an oral fluid sample is collected; and reading the presence or absence of the analyte from an indicator region on the apparatus.

This invention also provides kits for the detection of an analyte in an oral fluid. The kits include an apparatus for collection and lateral flow chromatography of an oral fluid as described herein and instructional materials describing the use of the apparatus.

Definitions

As used herein, the term "analyte" is used to refer to a moiety that is to be detected in a particular assay. Analytes can be atoms (elements), molecules, or groups of molecules. Analytes commonly detected in the assays of this invention include, but are not limited to, antibodies, antigens, growth factors, enzymes, therapeutic drugs, drugs of abuse, other ligands (e.g. protein A, avidin or biotin, conconavalin A, etc.), and the like. Particularly preferred analytes include antibodies and antigens relevant to infectious and non-infectious diseases, therapeutic drugs or drugs of abuse, and metabolites of the same.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially an Fab with part of the hinge region (see Fundamental Immunology, W. E. Paul, ed., Raven Press, N.Y. (1993) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or synthesized de novo using recombinant DNA methodologies.

The term "oral fluid", as used herein, refers to one or more fluids found in the oral cavity individually or in combination. These include, but are not limited to, saliva and mucosal transudate. It is recognized that oral fluid (e.g., saliva) can comprise a combination of fluids from a number of sources (e.g., parotid, submandibular, sublingual, accessory glands, gingival mucosa and buccal mucosa) and the term oral fluid includes the fluids from each of these sources individually, or in combination. The term saliva refers to a combination of oral fluids such as is typically found in the mouth, in particular after chewing. The term "mucosal transudate", as used herein, refers to fluid produced by the passive diffusion of serum components from oral mucosal interstitial into the oral cavity. Mucosal transudate often forms one component of saliva.

The terms "capillary matrix" or "porous matrix" are used herein to refer to a highly porous material characterized by a pore size sufficiently small that the material rapidly takes up aqueous solution (e.g., of oral fluid) predominantly by capillary action or "wicking".

The term "wick up" is used to refer to the uptake of a fluid predominantly by adsorption and capillary action.

A "lateral flow chromatography strip" refers to a test strip utilized for lateral flow chromatography. Lateral flow (chromatography) assays typically involve the application of a liquid test sample suspected of containing an analyte to be detected to an application zone of a lateral flow (immunochromatographic) test strip. The strip is comprised of a matrix material (e.g., paper, nitrocellulose, etc., see, e.g., U.S. Pat. No. 5,569,608) through which the test fluid and analyte suspended or dissolved therein can flow by capillary action from the application zone to a detection zone where a visible signal, or absence of such, reveals the presence or absence of the analyte. Where the detection of the analyte utilizes an antibody or antibody fragment, the assay may be referred to as a lateral flow immunochromatography assay and the strip a lateral flow immunochromatography strip.

A "receiving area or sample pad" of the lateral flow chromatography strip refers to the area of the lateral flow chromatography strip to which a sample is first applied.

A "signal" on the lateral flow chromatography strip refers to an indication, typically in a particular predefined region of the chromatography strip that indicates the presence or absence or quantity of analyte or the sufficiency of sample within the chromatography strip. The signal can be calorimetric, fluorescent, enzymatic, electroluminescent, radioactive, etc.

As used herein, "housing" refers to any member which encases or supports but does not react with the lateral flow chromatography strip.

As used herein, "cavity" refers to any receiving volume on or within the housing for holding the lateral chromatographic strip.

The "lateral flow chromatographic strip" is any absorbing member capable of transporting analyte and reagents to the visual inspection site. The strip can be nitro cellulose, cellulose acetate, paper, nylon, cellulose, glass fiber, polyester, or any other suitable bibulous material.

As used herein, an "immunoassay" is an assay that utilizes an antibody or antigen to specifically bind to the analyte. The immunoassay is characterized by the use of specific binding to a particular antibody as opposed to other physical or chemical properties to isolate, target, and quantify the analyte.

The phrase "specifically binds to an analyte" or "specifically immunoreactive with", when referring to an antibody refers to a binding reaction which is determinative of the presence of the analyte in the presence of a heterogeneous population of molecules such as proteins and other biologics (i.e., such as may be found in oral fluid). Thus, under designated immunoassay conditions, the specified antibodies bind to a particular analyte and do not bind in a significant amount to other analytes present in the sample. A variety of immunoassay formats may be used to select antibodies specifically immunoreactive with a particular analyte. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

A "label" is a composition detectable by spectroscopic, photochemical, biochemical, immunochemical, electrical, optical or chemical means. Useful labels in the present invention include magnetic beads (e.g., Dynabeads™.), fluorescent dyes (e.g., fluorescein isothiocyanate, Texas Red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold, silver, selenium, or other metals, or colored glass or plastic (e.g., polystyrene, polypropylene, latex, etc.) beads. Patents teaching the use of such labels include U.S. Pat. Nos. 3,817,837, 3,850,752, 3,939,350, 3,996,345, 4,277,437, 4,275,149, and 4,366,241. Means of detecting such labels are well known to those of skill in the art. Thus, for example, radiolabels may be detected using photographic film or scintillation counters, fluorescent markers may be detected using a photodetector to detect emitted illumination.

Enzymatic labels are typically detected by providing the enzyme with a substrate and detecting the reaction product produced by the action of the enzyme on the substrate, and colorimetric labels are detected by simply visualizing the colored label.

The term "subject", as used herein, refers to the test subject whose oral fluid is to be collected for testing. The subject includes without limitation to a person or a patient such as a mammal (e.g., a human).

The term "teeth", as used herein, refer to natural or prosthetic teeth of the subject. The teeth include, but are not limited to, the molars and/or the bicuspids.

DETAILED DESCRIPTION OF THE INVENTION

This invention provides a device for the rapid, one-step, collection and detection of analytes in oral fluid. In a preferred embodiment, the device is inserted into the oral cavity (e.g., preferably juxtaposed to the oral mucosa) where it absorbs oral fluid. After a period of time, the device is removed from the oral cavity and one or more indicators contained in the device are read out (e.g., by visual inspection or by detection in a "reader") to provide an indication of the presence or absence, and/or quantity of one or more analytes of interest. The device thereby provides a rapid, one-step, non-invasive assay for the detection of one or more analytes of interest.

The assay devices and methods of this invention can be used for the detection (positive or negative, and/or quantification) of virtually any analyte in oral fluid. Moreover, the devices and methods can be used to detect one or more analytes simultaneously. Such analytes may include, but are not limited to, antibodies to HIV, antibodies to HDTV, antibodies to *Helicobacter pylori*, antibodies to hepatitis, antibodies to measles, hepatitis antigens, antibodies to terponemes, antibodies to host or infections agents, cellular markers of pathology including, but not limited to, cardiolipin, lecithin, cholesterol, lipopolysaccharide and sialic acid, antibodies to mumps, antibodies to rubella, cotinine, cocaine, benzoylecgonine, benzodizazpines, tetrahydrocannabinol, nicotine, ethanol theophylline, phenyloin, acetaminophen, lithium, diazepam, nortriptyline, secobarbital, phenobarbital, theophylline, testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factors I and II, growth hormone release inhibiting factor, IGA, sex hormone binding globulin, glucose, cholesterol, caffeine, corticosteroid-binding globulin, PSA and DHEA-binding glycoprotein with the methods being particularly well suited to the detection of HIV antibodies.

Figure 1:
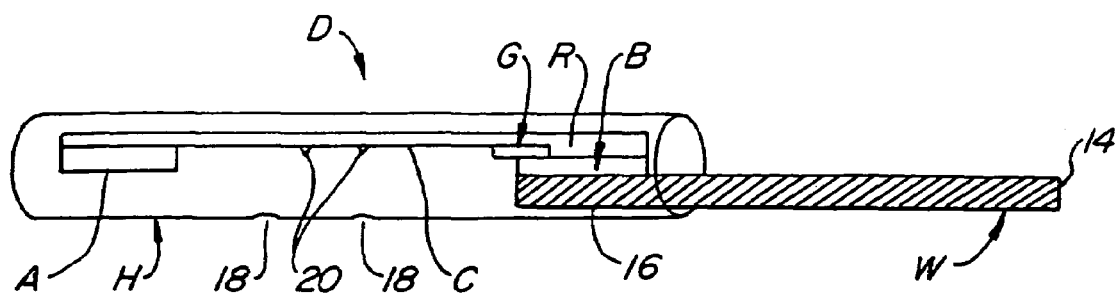
FIG. 1 is a partial cross-sectional schematic view of an oral collection device in accordance with an embodiment of the present invention.

The assay device of this invention relies on the unique cooperation between a capillary matrix (W in FIG. 1) and a lateral flow chromatographic strip (C in FIG. 1). The device is constructed such that the capillary matrix can be inserted into the oral cavity, and, in a preferred embodiment, juxtaposed to the oral mucosa. A bite plate coupled to the capillary matrix is insertable between the teeth of the patient to position the capillary matrix in the oral cavity (preferably in the buccal space) for receiving the oral fluid. The bite plate is typically held in place by the occlusal force of the teeth, preferably the molars and/or the bicuspids. In one preferred embodiment, where the assay device is oriented in the mouth such that the capillary matrix is situated between the gum and the cheek, an edge of the bite plate contacts the tongue when held between the teeth, and may include a saliva-stimulating substance for stimulating oral fluid production. The capillary matrix acts as a receiving body or pad that rapidly adsorbs (wicks up) oral fluid, e.g., via capillary action, and delivers that oral fluid to a lateral flow immunochromatography strip (e.g., C in FIG. 1). The immunochromatography strip then provides an indication of the presence, absence or quantity of one or more analytes in the oral fluid.

The device can be conveniently assembled such that the capillary matrix comprises a receiving pad for insertion into the oral cavity, while the lateral flow immunochromatography strip comprises the handle of the device. One or more zones on the handle can comprise indicators for readout (e.g., of a calorimetric signal) of the assay results. Of course, other formats of the device are suitable and will be readily recognized by those of skill in the art.

Capillary Matrix

The capillary matrix (porous matrix) material is preferably selected to provide a number of unique properties to the assay device. Such properties include, but are not limited to, a relatively low void volume, a pore size sufficient to provide rapid and effective delivery of the oral fluid to the test strip, low or non-reactivity with the oral fluid or analytes, easy release of the oral fluid to the immunochromatography test strip, and a non-deformable (when wetted) collection pad.

Because oral fluid may be in short supply (patients often suffer a "dry mouth" during testing) it is desirable to maximize the amount of oral fluid that is transported from the oral cavity (e.g., the oral mucosa) to the lateral flow chromatography strip. This is accomplished by the use of a capillary matrix having a minimum void volume. The capillary matrix should have a void volume less than about 65%/cm$^3$, preferably less than about 57%/cm$^3$, more preferably less than about 48%/cm$^3$, and most preferably less than about 40%/cm$^3$, 35%/cm$^3$, or even 25%/cm$^3$. Capillary matrices having such low void volumes typically deliver a significant amount of the absorbed oral fluid to the lateral flow chromatography strip.

The matrix itself must be of relatively small dimension. Specifically, the interstices are preferably of a dimension where capillary forces cause the fluid to be drawn into the capillary matrix. Thus, the capillary matrix is also selected to have an average pore size small enough to provide rapid uptake of the oral fluid with which it is contacted (e.g., via capillary action). The small pore size also functions to exclude particulate material present in the fluid sample. The pore size, however, is also selected to be large enough that the viscous oral fluid does not clog the capillary matrix and instead rapidly transports through the matrix to the lateral flow chromatography pad. Preferred materials have an average pore size that ranges from about 40 µm to about 250 µm, more preferably from about 60 µm to about 200 µm, and most preferably from about 80 µm to about 120 µm.

In addition to having a pore size (channel size) that results in rapid uptake of the oral fluid, the surfaces of the capillary matrix should be chemically compatible with rapid uptake of the oral fluid. Thus, preferred capillary matrix materials are themselves hydrophilic or treated to be hydrophilic (e.g., by addition of a surfactant also referred to as a detergent or wetting agent). That is to say, water must flow on and be attracted to the surfaces of these materials.

While a number of suitable materials are naturally hydrophilic (e.g., clean sintered glass or fused glass beads), other suitable materials (e.g., plastics) are typically hydrophobic (e.g., do not easily wet). However, such hydrophobic materials can be routinely treated with a wetting agent (i.e., surfactant/detergent) and thereby rendered hydrophilic (wettable). However, since the capillary matrix is used in the oral cavity, it is required that the treating detergent be known not to be harmful to the subject mammal (e.g., human body) and preferably be approved for such use by the relevant regulatory authority (e.g., Food and Drug Administration). In one preferred embodiment, a porous plastic material (e.g., polyethylene or polypropylene foam) can be rendered hydrophilic by taking the untreated matrix material and placing it in a dilute aqueous solution under vacuum, or a dilute alcoholic solution under ambient pressure, of an approved detergent such as sodium N-methyl cocoyl taurate. Thereafter, the treated material is dried, leaving the surfaces of the matrix apparently thinly coated with the detergent.

While N-methyl cocoyl taurate is preferred, it will be appreciated that other detergents can as well be used (e.g., N-methyl oleoyl taurate, sodium lauryl sulfate, Triton X 100). It is only required that the detergent be safe for mammalian oral exposure, not interfere with the test on the lateral chromatographic strip, and produce the required hydrophilic properties on the exterior surfaces of the matrix.

In addition to rapidly taking up and transporting the oral fluid to the lateral flow chromatography strip, the capillary matrix material is selected that preferably readily releases the fluid to the chromatography strip. This should be accomplished rapidly without compression of the matrix material itself. Thus, in a preferred embodiment, the capillary matrix delivers and releases oral fluid to the lateral flow chromatography strip with no manipulation (e.g., no squeezing or compression of the capillary matrix).

From the foregoing, it should be clear that preferred capillary matrix materials have an interstitial spacing that facilitates uptake of oral fluid through capillary attraction in combination with adsorption on the material. This causes the oral fluid gathered from the mouth to be transported to the lateral chromatographic strip in preference to remaining in the mouth. At the same time, when the oral fluid arrives at the lateral chromatographic strip, it is absorbed to the strip in preference to remaining in the capillary matrix.

In a preferred embodiment, the hydrophilic capillary matrix is an essentially nonabsorbing matrix which adsorbs liquid via capillary action. In such adsorption, the volume of the material is not appreciably effected. In addition, the capillary matrix material is relatively rigid such that its morphology remains essentially unchanged during the assay (e.g., when saturated with oral fluid). Thus, saturation of the matrix with an oral fluid does not substantially alter the average pore size or void volume of the porous matrix. In addition, saturation of the capillary matrix with an oral fluid results in a volume change of less than 30%, preferably less than 25%, more preferably less than 20% and most preferably less than about 15%, 10%, 5% or less than about even 1%.

In a particularly preferred embodiment, the capillary matrix can act as a barrier to back flow of reagents from the lateral flow chromatography strip back into the capillary matrix. This can be accomplished, for example, where the chromatography strip has a larger volume for fluid storage than the capillary matrix. In addition or alternatively, where the lateral flow chromatography strip is more hydrophilic than the capillary matrix the capillary matrix can also act as a barrier to backflow.

The capillary matrix materials are selected such that they are not chemically reactive with either the oral fluid or the analytes contained therein. Matrix materials compatible with oral fluid are well known to those of skill in the art and include, but are not limited to, glass, resins, and various plastics.

In one preferred embodiment, the properties described above are achieved by the use of porous plastic materials for the capillary matrix. Suitable porous plastic materials include, but are not limited to, porous matrices of high density polyethylene (HDPE), ultra-high molecular weight polyethylene (UHMW), polypropylene (PP), polyvinylidene fluoride (PVDF), polytetrafluoroethylene (PTFE), polyester, nylon 6 (N6) and polyethersulfone (PES). In a preferred embodiment, the porous matrix materials are either themselves hydrophilic (so as to readily uptake the oral fluid) or are treated (e.g., with a surfactant/detergent) so as to be hydrophilic.

Such porous plastics are commercially available (see, e.g., Porex Technologies, Fairbum, Ga.). Particularly preferred porous plastics are detergent (surfactant) treated polyethylene and/or polypropylene. The treatment typically involves soaking the capillary matrix in a surfactant/detergent and then allowing it to dry naturally or force drying the material.

Particularly preferred porous matrix materials are Porex7 X-4588, 80-120 µm pore size at 0.024 inch of thickness made from polypropylene. Likewise, Porex7 X-4903 at 0.0625 inch, pore size 45-90 µm, and Porex7 X-4913 at 0.0625 inch, pore size 90-130 µm, are suitable. In one preferred embodiment, these materials are treated with sodium N-methyl cocoyl taurate. The capillary matrix materials are soaked in the detergent which is then dried onto the surfaces.

It will be understood that the Porex7 material that are utilized do not retain large volumes of the oral fluid. For example, consider the following data:

TABLE 1

Void volume of Porex7 X-4903
Medium Pore
Porex7 X-4903 1 cm × 1 cm × 0.1588 cm

| # | Dry Weight (g) | Weight + $H_2O$ (g) | Weight of $H_2O$ (g) | % Volume/$cm^3$ |
|---|---|---|---|---|
| 1 | 0.0791 | 0.1595 | 0.0804 | 50.63 |
| 2 | 0.0745 | 0.1480 | 0.0735 | 46.28 |
| 3 | 0.0746 | 0.1480 | 0.0734 | 46.22 |
| 4 | 0.0767 | 0.1503 | 0.0736 | 46.35 |
| 5 | 0.0762 | 0.1503 | 0.0741 | 46.66 |
| | | Average | 0.0750 | 47.23 |

TABLE 2

Void volume of Porex7 X-4913.
Coarse Pore
Porex7 X-4913 1 cm × 1 cm × 0.1588 cm

| # | Dry Weight (g) | Weight + H$_2$O (g) | Weight of H$_2$O (g) | % Volume/cm$^3$ |
|---|---|---|---|---|
| 1 | 0.0782 | 0.1670 | 0.0888 | 55.92 |
| 2 | 0.0803 | 0.1723 | 0.0920 | 57.93 |
| 3 | 0.0806 | 0.1700 | 0.0894 | 56.30 |
| 4 | 0.0851 | 0.1818 | 0.0967 | 60.89 |
| 5 | 0.0747 | 0.1593 | 0.0846 | 53.27 |
|   |        | Average | 0.0903 | 56.86 |

Above, we assume that 1 cm$^3$ 1 ml 1 g H$_2$O.

At the same time, hydrophilic capillary matrix does not have a high relative retention of the oral fluid. For example, it readily surrenders its fluid to lateral chromatographic strip and absorbent pad (A in FIG. 1). It will be understood that hydrophilic capillary matrix acts more as a conduit than as an absorbent; material is readily discharged from the wick or capillary matrix.

Identification of Suitable Porous Matrix Materials

It will be appreciated that the rate of oral fluid uptake, transport to the lateral flow chromatography pad and release to the pad is a function of both the composition of the capillary matrix and its shape (e.g., area exposed to the oral mucosa, cross-sectional area, and area contacted to the lateral flow chromatography strip. The rates are also effected by the average pore size, hydrophilicity of the capillary matrix material and the relative absorbance characteristics of the capillary matrix and the lateral flow chromatography pad.

These parameters can be optimized according to routine methods well known to those of skill in the art. In one embodiment, this is accomplished by assembling a test device having the desired capillary matrix material and lateral flow immunochromatography strip. The test device can then be contacted with a test oral fluid solution (e.g. natural oral fluid, or synthetic oral fluid, see U.S. Pat. No. 5,695,929 and copending U.S. Ser. No. 08/608,431).

The contacting can be accomplished by actual insertion of the receiving portion (e.g., receiving pad/face) of the capillary matrix into an oral cavity and contact with an oral mucosa (e.g., of a human or non-human test animal). Alternatively, the contacting can be accomplished by touching the capillary matrix with the test fluid disposed on a surface or in a bowl or other receptacle, immersing part or all of the capillary matrix in the test fluid, or contacting the capillary matrix with a test body (e.g., a sponge, cloth, swab, etc.) impregnated with the test fluid.

The test oral fluid will typically be contacted with the capillary matrix for the time period it is desired to run the assay (e.g., less than 5 minutes) and then the lateral flow chromatography strip can be read for the presence, absence or quantity of analyte and/or for the amount of oral fluid taken up. In this manner it will be determined if the assay gives adequate sensitivity and specificity.

In addition, the time period for uptake of oral fluid into the capillary matrix, and lateral flow chromatography strip can be determined. Similarly the total volume of sample required to properly saturate the lateral flow chromatography strip and the amount of fluid retained by the capillary matrix can also be ascertained (e.g., by weighing the various components before and after the assay).

In a preferred embodiment, the capillary matrix, when inserted and held in a mouth is saturated with oral fluid in under about 5 minutes, preferably in under about 3 minutes, more preferably in under about 1 minute, and most preferably in under about 30 seconds. Similarly, the capillary matrix will release sufficient fluid to the chromatography strip for a properly run assay (an assay run to the specifications of the chromatography strip) in under about 10 minutes, preferably in under about 5 minutes, more preferably in under about 3 minutes and most preferably in under about 2 minutes or even in under about 1 without compression of the porous matrix.

A porous matrix will be made that is saturated by less than about 500 μL, more preferably by less than about 500 μL, preferably by less than about 300 μL, more preferably by less than about 200 μL and most preferably by less than about 100 μL.

It will be recognized that where just the oral fluid uptake and release properties are to be assayed, there is no need to utilize a complete chromatographic assay. The base capillary matrix material, lateral flow chromatography strip, and if desired, blocking pad, materials can be assembled. The rate of fluid uptake and delivery to the pad can be quantified by immersing or contacting the capillary matrix pad with a sample fluid (e.g., natural or synthetic oral fluid) and quantifying the rate of fluid uptake and delivery to the pad and/or the amount retained within the capillary matrix (e.g., by weighing the various elements after particular preselected times of exposure to the test fluid). A combination of materials and shapes elements that provides maximal fluid delivery of an oral fluid from an oral mucosa to the lateral flow chromatography strip in the shortest amount of time is preferred.

In one particularly preferred embodiment, the lateral flow chromatography strip is a nitrocellulose strip (e.g., Syntron QuickScan 6, Syntron Bioresearch, Carlsbad, Calif.; Avitar Visualine II, Avitar Technologies, Canton, Mass.; Determine HIV-1/2, Abbott Laboratories, Abbott Park, Ill.). A typical chromatographic strip is Millipore SRHF or STHF nitrocellulose membrane (Millipore Corp., Bedford, Mass.) having dimensions 4 mm×0.50 mm. A porous matrix material measures 7 mm×0.52 mm (0.0625 inch thick) and overlaps the nitrocellulose membrane by about 64 mm$^2$. In another embodiment, the capillary matrix is paddle-shaped having a total surface area of about 720 mm$^2$ and overlapping the chromatographic strip by about 8 mm$^2$. The small overlap is particularly well-suited to embodiments containing a conjugate pad (G in FIG. 1) as it serves to effectively channel the oral fluid through the conjugate pad. In yet another embodiment, the capillary matrix is also paddle-shaped, but has a narrow handle portion widening to a relatively short head portion. The total surface area of the capillary matrix is less than about 720 mm$^2$ because of the narrow handle portion, and is typically less than about 400 mm$^2$.

Lateral Flow Chromatography Strip

The assay device of this invention can utilize virtually any lateral flow chromatography strip for detection and/or quantification of the analyte or analytes. Lateral flow chromatography assays are well known to those of skill in the art (see, e.g., U.S. Pat. Nos. 5,569,608, 5,120,643, 5,656,503, 4,855, 240, and 5,591,645, British Patent GB 2204398A, and European patent EP 0323605 B1) and such assays are commercially available on a retail or OEM basis for numerous analytes.

Lateral flow immunoassays typically involve the application of a liquid test sample suspected of containing an analyte to be detected to an application zone of a lateral flow (immunochromatographic) test strip. The strip is comprised of a matrix material (e.g., paper, nitrocellulose, etc., see, e.g., U.S. Pat. No. 5,569,608) through which the test fluid and analyte suspended or dissolved therein can flow by capillarity from the application zone to a detection zone where a visible signal, or absence of such, reveals the presence or absence of the analyte.

Typically, the strip will include means for immunospecifically binding the analyte to be detected with its specific binding partner (e.g., where the analyte is an antigen, the binding partner is an antibody or antibody fragment, and vice versa) which bears a detectable label. In one such scheme, as disclosed in U.S. Pat. No. 4,446,232, the strip contains an enzyme labeled, mobile binding partner for the analyte which is in a zone downstream from the sample application zone. If analyte is present in the test sample, it will combine with its labeled binding partner to form a complex which will flow along the strip to a detection zone which contains a substrate for the enzyme label capable of providing a signal (e.g., a colored response) in the presence of the enzyme label.

The strip typically contains a zone in which analyte is immobilized, so that the labeled binding partner which does not combine with analyte, due to absence of analyte in the sample, will be captured and thereby inhibited from reaching the detection zone. There have been published various modifications of this technique, many of which involve some competitive specific binding system in which the presence or absence of analyte in the test sample is determined by the detection or lack thereof of labeled binding partner in the detection zone. In U.S. Pat. No. 4,868,108 there is disclosed a similar scheme with the addition of an immobilized capture reagent for the enzyme labeled binding partner in the detection zone to concentrate the enzyme label and enhance its ability to react with the enzyme substrate and thereby render the assay more sensitive.

Not all of the schemes for immunochromatography rely on an enzyme labeled binding partner/enzyme substrate as providing the signal for detection of the analyte. In U.S. Pat. No. 4,806,311 there is disclosed a multizone test device for the specific binding assay determination of an analyte and an immobilized binding partner therefore together with a detection zone for receiving labeled reagent which migrates thereto from the reagent zone. The detection zone contains an immobilized form of a binding substance for the labeled reagent. The labeled reagent bears a detectable chemical group having a detectable physical property which is detectable on the basis of its own physical properties, so that it does not require a chemical reaction with another substance. Exemplary of such groups are colored species fluoresces, phosphorescent molecules, radioisotopes and electroactive moieties. U.S. Pat. No. 4,313,734 describes the use of gold sols as labels for antibodies which are detectable without a chemical change.

Many lateral flow immunochromatography systems utilize particulate (microparticle) markers (e.g., gelatin, dyed latex, or colloidal gold) which are labeled with a binding partner (e.g., antibody or antigen) that binds the analyte of interest.

The microparticles or other detectable moieties attached to an analyte binding moiety (e.g., an antibody or antigen) are dried onto (or otherwise localized in) either a lateral flow chromatographic strip or onto a sample application pad (typically glass fiber) which in turn is affixed to one end of a strip of chromatographic medium such as nitrocellulose. Another material binding to the analyte of interest is affixed to the chromatographic medium at or near the end opposite to the end having the application pad.

The liquid sample to be analyzed is placed on the pad, causing the suspension of the microparticles into the liquid and allowing any analyte in the liquid sample to bind to the analyte-binding material attached to the microparticles. The liquid sample leaves the application pad by diffusion and capillary action and begins to migrate along the nitrocellulose strip carrying the microparticles down the strip along with the liquid. When the liquid containing the suspended microparticles arrives at the region of the chromatographic strip bearing the second binding material, the analyte (if present in the original sample) will form a molecular bridge between the analyte-binding material on the microparticles and the analyte-binding material affixed to the strip, resulting in the immobilization of the microparticles at that point on the strip where the analyte-binding material is affixed. This immobilization of the microparticles results in a visible signal (e.g., a colored band or dot) at this point on the strip. If the analyte is not present in the sample, the microparticles will continue past this location on the chromatographic strip and a visible signal will not be produced.

It will be appreciated that other labels (e.g., fluorescent labels) besides microparticles can be utilized. In addition, a single chromatography strip can contain reagents to detect or quantify a number of different analytes.

It will also be appreciated that the lateral flow strip can use an analyte detection that does not involve an antibody-antigen recognition system. Thus, for example, the strip can be impregnated in a detection zone with a chemical that reacts with the analyte itself to produce a signal.

The devices of this invention can be readily assembled with any of a variety of commercially available lateral flow chromatography assays (e.g., Syntron QuickScan 6, Syntron Bioresearch, Carlsbad, Calif.; Avitar Visualine II, Avitar TEchnologies, Canton, Mass.; Determine HIV-1/2, Abbott Laboratories, Abbott Park, Ill.).

Optional Blocking Strip

The assay devices of this invention can optionally include a blocking strip between the porous matrix and the lateral flow chromatography strip. The blocking strip can be impregnated with buffers to adjust the pH (e.g., to pH 7.5) of the oral fluid for compatibility with the lateral flow chromatography assay. The blocking strip can also include one or more blocking reagents that reduce non-specific binding of the analyte and/or reagents of the assay device and thereby reduce the occurrence of false positives. Suitable blocking reagents include, but are not limited to, bovine serum albumin (BSA), deoxycholate, and n-lauroyl sarcosine. In one particularly preferred embodiment, the blocking solution includes: 4% polyvinyl alcohol (10 Kid MW, Aldrich 36,062-2), 4% sodium-n-lauroylsarcosine (Sigma L5777), 2% polyvinyl pyrrolidone (10 Kd MW, Sigma P2263) in 60×. Tris EDTA (Sigma T9285) or 7.5% sodium-n-lauroylsarcosine (Sigma L5777), 2.5% tectonic 1307 (BASF), 0.00001% polyethyleneglycol compound (Sigma P2263) in 100× Tris EDTA buffer (Sigma T9285).

The blocking pad can be composed of a wide variety of materials as long as they do not impede flow of oral fluid from the capillary matrix to the lateral flow chromatography strip. Such materials include, but are not limited to, paper, cellulose, nitrocellulose, polyester, glass fiber, and the like. Particularly preferred materials will be selected to reduce or eliminate backflow of reagents or oral fluid from the chromatographic test strip to the capillary matrix.

It is noted that the blocking agents can be placed on the capillary matrix instead or, or in addition to, their placement on the optional blocking strip. In some configurations the blocking agents are on the capillary matrix, and in some other configurations, both the blocking agents and the conjugate are on the capillary matrix.

Optional Conjugate Strip

In one embodiment, the lateral flow chromatography reagents (e.g., antibody labeled gold particles, etc.) are disposed in the lateral flow chromatographic strip itself, and/or directly in the capillary matrix. In another embodiment, however, one or more chromatography reagents can be disposed in a conjugate strip (G in FIG. 1), e.g., to facilitate fabrication. The conjugate strip is positioned juxtaposed to the lateral flow chromatography strip such that the oral fluid must pass across or though the conjugate strip in order to migrate up the chromatographic strip. Alternatively, the conjugate strip can be woven into the lateral flow chromatography strip or can be placed in-line, in the same place, as the lateral flow chromatography strip. As with the blocking strip, the conjugate strip can be fashioned out of any convenient material (e.g., nitrocellulose) that is compatible with the assay and that does not substantially impede flow of the oral fluid and reagents. In a preferred embodiment, the conjugate pad is a 4 mm×4 mm glass fiber pad or a polyester pad (e.g., Ahlstrom Remay #2033).

Assembly of the Assay Device

The components (e.g., capillary matrix, lateral flow chromatography strip, optional blocking strip) can be assembled by any of a wide variety of means well known to those of skill in the art. Thus, for example, the components can be welded together or glued together and the like.

In a preferred embodiment, the components are simply pressed together and held in place by a housing (H). Housing (H) can be of any desired construction. For example, in prototype construction, soda straws are utilized which supplied both adequate structure and visibility to gauge accuracy of testing. Acrylic tubing has also been used. In addition, polyethylene, mylar, or other films can be used if they are adequate to provide minimal support to the strip and protect the strip from exposure to the oral fluid except via the capillary matrix. It will be recognized that other stock tubing materials can be used or specially designed housings can be custom molded or extruded.

The components are assembled such that the lateral flow chromatography strip is disposed lengthwise within the straw and appressed at one end to an end of the capillary matrix (W). The housing (H) thus provides a convenient handle for insertion of the capillary matrix into the oral cavity of a mammal (e.g., a human).

Figure 2:
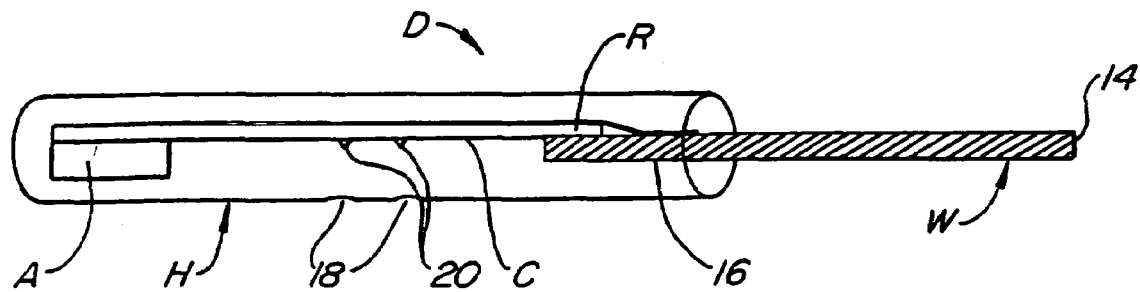
FIG. 2 is a partial cross-sectional schematic view of an oral collection device in accordance with another embodiment of the present invention.
Figure 3:
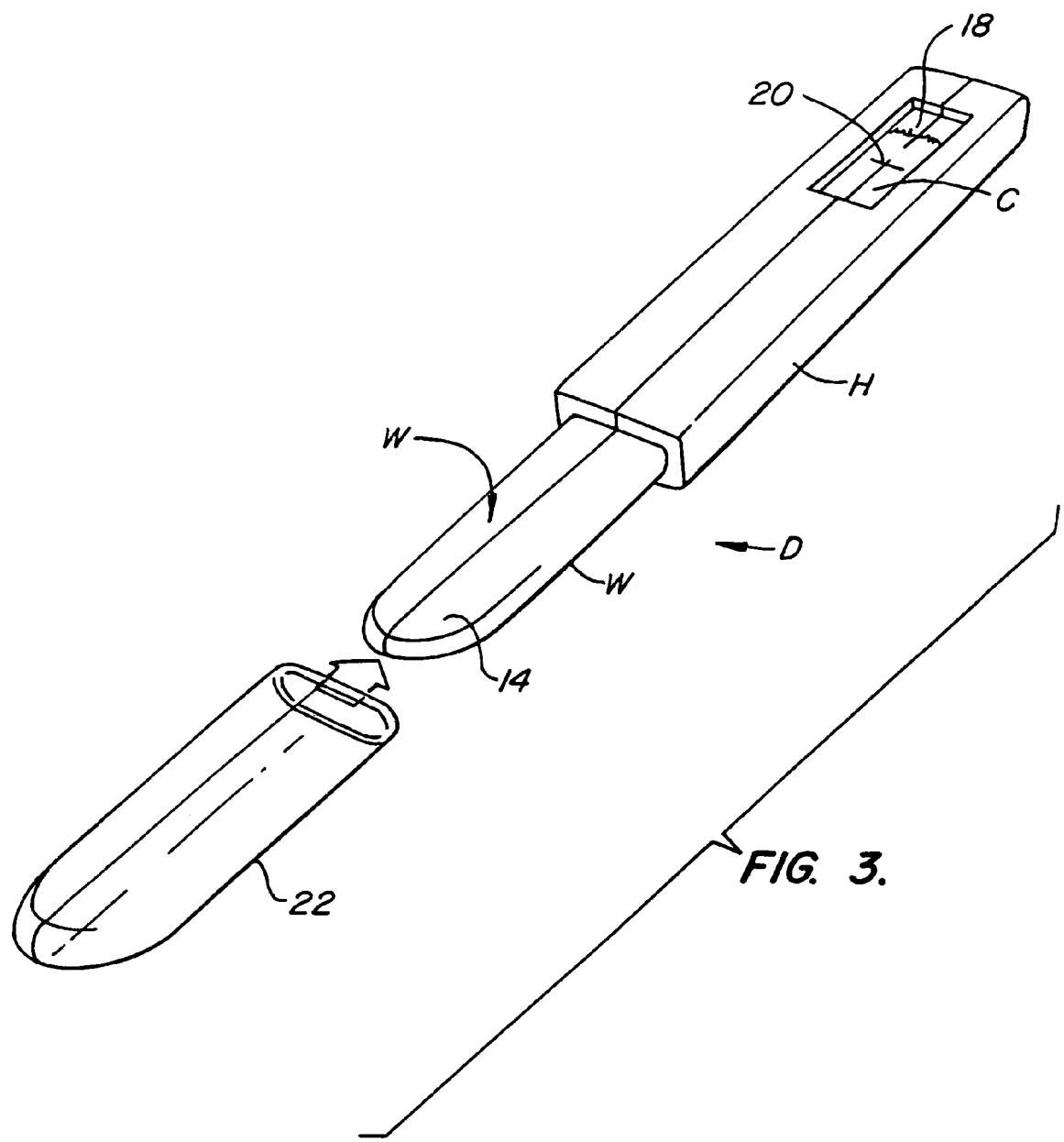
FIG. 3 is a perspective view of the exterior of an oral collection device in accordance with another embodiment of the present invention.

FIGS. 1, 2, and 3 illustrate various embodiments of the assay device (D) of this invention. Lateral flow chromatography or immunochromatography strip (C) is disposed lengthwise within housing (H). One end of the chromatography strip (C) contacts directly, or by way of blocking pad (B) with a portion of one end (16) of capillary matrix (W). The capillary matrix (W) projects out of the housing (H) at another end (14) where it presents a face (3) that acts as an adsorbent surface for uptake of oral fluid. The oral fluid migrates through the matrix (W) and through blocking pad (B) if present, where it is finally delivered to a receiving area (R) on the lateral flow chromatographic strip (C). The test easily lends itself to saliva stimulation—such as by placing slightly acidic compounds at the end (14) of the wick or capillary matrix (W).

The oral fluid then migrates along the lateral flow chromatography strip (C) where it interacts with various reagents (e.g., antibody or antigen labeled binding partners (e.g., antibodies or antigens)) that are deposited within the chromatography strip (C) and/or within optional conjugate pad (G) which, when present, contacts the chromatography strip (C).

The oral fluid/reagent combination continues to migrate along the chromatography strip (C) until it reaches one or more indicator zones (20). If an analyte is present the indicator zone (20) immobilizes the bound labeled analyte or otherwise produces a detectable signal. One of more of the indicator zones can optionally indicate sample sufficiency (e.g., with a color change) when the necessary sample volume and/or analyte concentration is reached. Sample sufficiency indicators are well known to those of skill in the art and particular advantageous sample sufficiency indicators are described in copending application U.S. Ser. No. 08/456,459 and in U.S. Pat. No. 5,479,937.

The indicator zones (20) can be read (e.g., via visual inspection or other means) through view ports (18). As mentioned above, the device is optionally equipped with blocking pad (B). This pad can be impregnated with a blocking reagent (e.g., n lauryl sarcosine) and/or buffer(s) for adjusting pH of the sample. In addition, the blocking pad (B) can be fashioned out of a semi-permeable material that allows oral fluid flow towards the chromatography strip (C), but prevents backflow of oral fluid and/or reagents into the capillary matrix (W). Further, the far end (away from the capillary matrix) of the chromatography strip (C) can bear affixed thereto an absorbent pad (A) which acts as a reservoir to receive the oral fluid and thereby prevent backflow into the capillary matrix (W).

It will be appreciated that the devices can be assembled in a wide variety of forms. One preferred embodiment is illustrated in FIG. 3. In this embodiment, the lateral flow chromatography strip (C) is disposed within a housing (H) that acts as a handle for manipulating the device. The housing/handle (H) is provided with viewports (18) for visualizing sample sufficiency and assay results. The capillary matrix (W) protrudes out from the housing (H) at the end (14) to provide a planar surface for insertion into the oral cavity where the capillary matrix face (3) can be contacted to the oral mucosa.

For convenience, the assay device can be optionally equipped with a cover (22) for protection of the capillary matrix surface (3) before and after use. This prevents contamination of the assay device and facilitates sanitary disposal of used devices.

Figure 4:
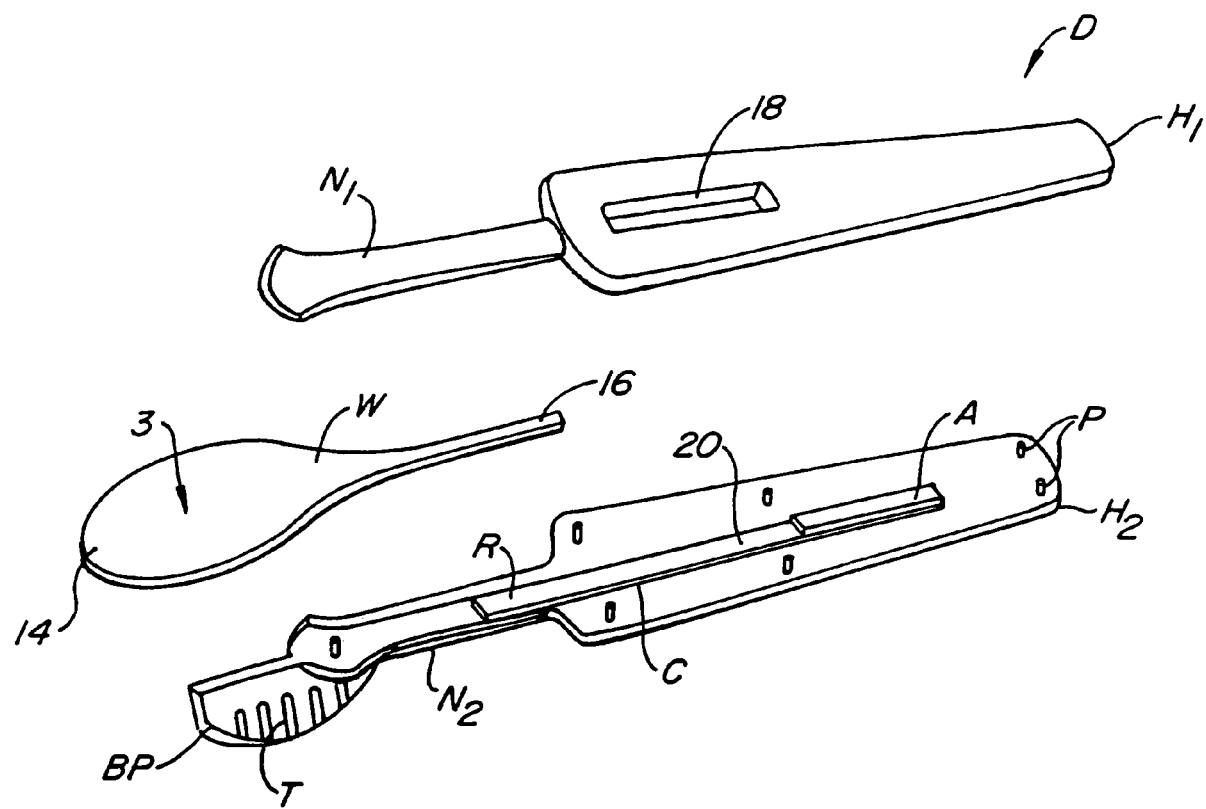
FIG. 4 is an exploded perspective view of an oral collection device in accordance with another embodiment of the present invention.

FIG. 4 illustrates another construction of the device (D) which includes a housing formed by an upper housing ($H_1$) portion and a lower housing portion ($H_2$). The two housing portions are easily and detachably snapped together using pins (P) in lower housing portion ($H_2$) and corresponding apertures (not shown) in upper housing portion ($H_1$). In this embodiment, a lateral flow chromatography strip (C) and an absorbent pad (A) are disposed within a cavity formed between the upper and lower housing portions. The upper housing portion ($H_1$) includes viewport (18) for visualizing sample sufficiency and assay results in the indicator zone(s) (20) of the chromatography strip (C). The chromatography strip (C) has a receiving area (R) for receiving the oral fluid that migrates through the capillary matrix (W) in the direction from one end (14) protruding from the housing to the other end (16) inserted into the housing. In this embodiment, the capillary matrix (W) is paddle-shaped extending from a narrow handle portion at the end (16) widening to a relatively short head portion at the end (14) which presents a face (3) that acts as an adsorbent surface for uptake of oral fluid. The narrow handle portion at the end (16) of the capillary matrix (W) is held in an elongated neck of the housing defined by upper neck portion ($N_1$) of upper housing portion ($H_1$) and lower neck portion ($N_2$) of lower housing portion ($H_2$). The total surface area of the capillary matrix (W) is typically less than about 600 mm (e.g. less than about 400 $mm^2$ in one specific embodiment).

The device (D) of FIG. 4 includes an optional bite portion (BP) coupled to the capillary matrix (W). The bite portion (BP) is insertable between the teeth of the subject to be tested to position the capillary matrix conveniently in place for collecting oral fluid. The bite portion (BP) may have various configurations. In the embodiment shown, the bite portion is formed as a bite plate (BP) having a curved edge and being connected or integrally formed with the lower neck portion ($N_2$) of the lower housing portion ($H_2$). The bite plate (BP) is held in place by the occlusal force of the teeth (preferably the molars and/or the bicuspids) to position the capillary matrix (W) in the oral cavity (preferably in the buccal space) for receiving the oral fluid. In this embodiment, the bite plate (BP) is substantially perpendicular to the capillary matrix (W), although an angle of incline can be formed therebetween in other embodiments. The bite plate (BP) desirably includes upper and lower optionally textured (e.g. grooved) surfaces (T) that can be easily secured between the teeth to hold the device (D) in place for oral fluid collection. The upper textured surface (T) shown includes a plurality of transverse grooves and/or ridges. The bite plate (BP) advantageously contacts the tongue of the subject with its edge when held between the teeth. The bite plate (BP) may include a saliva-stimulating substance (e.g., acid, salt, sugar, as described herein, etc.) for stimulating oral fluid production, as facilitated by its contact with the tongue. The bite plate (BP) may be made of a variety of materials, such as plastic.

The reader will understand that with the interaction of hydrophilic capillary matrix (W) and lateral chromatographic strip (C), an extremely simple construction is possible. Further, the end product operates in a manner not unlike a conventional thermometer. The test is fast—with prototypes exhibiting about 2 minutes for complete test results.

Most importantly, the test only requires minimal volumes of fluid from the oral cavity to run a test. For example in the designs shown, the assays utilized only 100 to 200 µL of oral fluid. This is an improvement of at least a factor of 4 over the sample volume requirements of previous assays.

Use of the Assay Device

In use, the assay device of this invention is inserted into the oral cavity of a mammal (e.g., a human, or in veterinary or research applications, a non-human) such that the handle within which is disposed the chromatography strip is outside the mouth. The capillary matrix face (3) is preferably contacted to the oral mucosa and, in a particularly preferred embodiment, is pressed to the oral mucosa at the gingival crest e.g., pressed between the cheek and the gums.

In one preferred method of use, the assay device is kept in place, without mastication, until sufficient sample is collected. This can be for a predetermined time interval or until the capillary matrix achieves a characteristic tactile quality, or appearance of a signal indicator (e.g., a color change in a test window) indicates an adequate sample.

At the recommended time (after completion of the immunochromatography assay), the device is read (e.g., by visual inspection of the indicator zone(s) through the viewport(s)), to determine whether the subject is positive or negative for the analyte(s) of interest or to quantify the analyte(s).

Kits for the Detection of Analytes in Oral Fluids

In another embodiment, this invention provides kits for the detection of one or more analytes in oral fluids. The kits include one or more of the assay devices described herein. In addition, the kits may include instructional materials containing directions (i.e., protocols) for the practice of the assay methods of this invention. While the instructional materials typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to Internet sites that provide such instructional materials.

The kits may optionally contain any of the buffers, reagents, detection reagents, and so forth that are useful for the practice of the methods of this invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated in their entirety by reference for all purposes.

What is claimed is:

1. A method for rapid collection and assay of oral fluids, comprising the steps of:
   (a) placing an assay device into an oral cavity, said assay device comprising:
      (i) an assay portion housing a lateral flow assay strip, said lateral flow assay strip containing at least one reagent that is used to detect one of the presence or absence of at least one analyte in a fluid;
      (ii) a neck portion extending from said assay portion, said neck portion forming a channel for delivery of fluid to said assay strip and said channel being defined by a first, narrow part proximal to the assay portion and a second part including an opening for receiving the oral fluid, wherein said second part includes a channel width that is substantially wider than the channel width at the narrow end;
      (iii) a collection strip in fluid communication with said lateral flow assay strip, said collection strip having a first portion disposed within the channel and a second portion protruding outwardly from the neck portion opening; and
      (iv) a blocking strip coupled between and in flow communication with said lateral flow assay strip and said collection strip;
   (b) removing said assay device from said oral cavity; and
   (c) determining the presence or absence of at least one analyte.

2. The method of claim 1, wherein said fluid source is an oral cavity.

3. The method of claim 1, wherein said collection strip comprises a capillary matrix adapted for rapid wicking of fluid from a fluid source to the assay strip.

4. The method of claim 1, wherein said second portion of the collection strip is one of a paddle-shape and a substantially bulbous shape.

5. The method of claim 1, wherein said second portion of said collection strip is paddle-shaped.

6. The method of claim 1, wherein the width of said neck portion tapers from the opening width to the narrow end width.

7. The method of claim 1, wherein said lateral flow assay strip is an immunochromatography strip.

8. The method of claim 1, wherein said reagent is a binding partner which bears a detectable label.

9. The method of claim 8, wherein said reagent is a label comprised of a colloidal gold particle.

10. The method of claim 9, wherein said colloidal gold particle is gold sol.

11. The method of claim 8, wherein said reagent is an enzyme labeled binding partner.

12. The method of claim 1, wherein said reagent comprises one of an antigen and an antibody.

13. The method of claim 1, wherein said blocking strip contains at least one blocking agent or a buffer.

14. The method of claim 1, wherein said collection strip is adsorbent.

15. The method of claim 1, wherein said blocking strip contains a blocking agent or a buffer.

16. The method of claim 15, wherein said buffer is to adjust the pH of the oral fluid sample.

17. The method of claim 15, wherein said lateral flow assay strip further comprising a conjugate strip coupled between and in flow communication with the blocking strip and the lateral flow assay strip, wherein said conjugate strip contains a labeled binding partner for at least one type of antibody in the oral fluid.

18. The method of claim 1, wherein said lateral flow assay strip further comprising a conjugate strip coupled between and in flow communication with the collection strip and the lateral flow assay strip, wherein the conjugate strip contains a labeled binding partner for at least one type of antibody in the oral fluid.

19. The method of claim 1, wherein said analyte is at least one of an atom, a molecule, or a group of molecules.

20. The method of claim 1, wherein said analyte is at least one of an antibody, an antigen, a growth factor, an enzyme, a therapeutic drug, a drug of abuse, or a ligand.

21. The method of claim 1, wherein said analyte is selected from the group consisting of antibodies to HIV, antibodies to HTLV, antibodies to *Helicobacter pylori*, antibodies to hepatitis, antibodies to measles, antibodies to mumps, antibodies to rubella, cotinine, cocaine, benzoylecgonine, benzodiazepine, tetrahydrocannabinol, nicotine, ethanol theophylline, phenyloin, acetaminophen, lithium, diazepam, nortryptyline, secobarbital, phenobarbitol, theophylline, testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factors I and II, growth hormone release inhibiting factor, IGA, sex hormone binding globulin, glucose, caffeine, cholesterol, corticosteroid binding globulin, PSA, DHEA binding glycoprotein and combinations thereof.

22. The method of claim 1, wherein said oral fluid contains at least one of salivary fluids or mucosal transudate.

23. The method of claim 1, wherein said assay device is placed against or wires around the oral mucosa in said oral cavity at the gingival crest or gingival base.

24. An assay method for HIV using oral fluids, comprising the steps of:
   (a) placing an assay device into an oral cavity, said assay device comprising:
      (i) an assay portion housing a lateral flow assay strip, said lateral flow assay strip containing at least one reagent that is used to detect one of the presence or absence of at least one HIV antibody in the fluid;
      (ii) a neck portion extending from said assay portion, said neck portion forming a channel for delivery of fluid to said assay strip and said channel being defined by a first, narrow part proximal to the assay portion and a second part including an opening for receiving the oral fluid, wherein said second part includes a channel width that is substantially wider than the channel width at the narrow end;
      (iii) a collection strip in fluid communication with said lateral flow assay strip, said collection strip having a first portion disposed within the channel and a second portion protruding outwardly from the neck portion opening; and
      (iv) a blocking strip coupled between and in flow communication with said lateral flow assay strip and said collection strip;
   (b) removing the assay device from the oral cavity; and
   (c) determining the presence or absence of HIV antibodies.

25. The method of claim 24, wherein said oral fluid contains at least one of saliva or mucosal transudate.

26. The method of claim 24, wherein said assay device is placed against the oral mucosa in an oral cavity at the gingival crest or gingival base.

* * * * *